United States Patent [19]

Wehinger et al.

[11] 4,162,321
[45] Jul. 24, 1979

[54] SULPHUR-CONTAINING AMINO-DIHYDROPYRIDINES, AND THEIR USE AS MEDICANTS

[75] Inventors: Egbert Wehinger, Velbert; Friedrich Bossert, Wuppertal; Horst Meyer, Wuppertal; Gerhard Franckowiak, Wuppertal; Wulf Vater, Leverkusen; Arend Heise, Wuppertal; Stanislav Kazda, Wuppertal; Kurt Stoepel, Wuppertal, all of Fed. Rep. of Germany

[73] Assignee: Bayer Aktiengesellschaft, Leverkusen, Fed. Rep. of Germany

[21] Appl. No.: 828,137

[22] Filed: Aug. 26, 1977

[30] Foreign Application Priority Data

Sep. 2, 1976 [DE] Fed. Rep. of Germany ....... 2639498

[51] Int. Cl.² .................... C07D 213/55; A61K 31/34
[52] U.S. Cl. .................................... 424/266; 546/294; 546/297; 546/322
[58] Field of Search ................ 424/266; 260/294.8 F, 260/294.8 G, 295.5 R; 546/294, 297

[56] References Cited

U.S. PATENT DOCUMENTS 4,017,629  4/1977  Habicht et al. ...................... 424/266

*Primary Examiner*—Alan L. Rotman
*Attorney, Agent, or Firm*—Sprung, Felfe, Horn, Lynch & Kramer

[57] ABSTRACT

The invention relates to new dihydropyridines which are substituted by an amino group in at least one of the 2- and 6-positions, by a sulphur-containing substituent in the 3-position, by a cyclic substituent in the 4-position and by a carbonyl substituent in the 5-position. The new dihydropyridines are particularly useful as agents which influence the circulatory system. Also included in the invention are procedures for preparation of the new dehydropyridines, compositions containing them and methods for their use.

11 Claims, No Drawings

SULPHUR-CONTAINING AMINO-DIHYDROPYRIDINES, AND THEIR USE AS MEDICANTS

The present invention relates to new sulphur-containing amino-dihydropyridines, several processes for their preparation and their use as medicaments, in particular as agents which influence the circulatory system.

It has already been disclosed that 2,6-dimethyl-4-phenyl-1,4-dihydropyridine-3,5-dicarboxylic acid diethyl ester is obtained when benzylideneacetoacetic acid ethyl ester is reacted with β-amino-crotonic acid ethyl ester or acetoacetic acid ethyl ester and ammonia (Knoevenagel, Ber. dtsch. chem. Ges. 31, 743 (1898)).

Furthermore, it is known that certain 1,4-dihydropyridines have interesting pharmacological properties (F. Bossert and W. Vater, Naturwissenschaften 58, 578 (1971)).

The invention relates to new sulphur-containing amino-dihydropyridines of the formula I, which can exist in three tautomeric forms I(a) to (c):

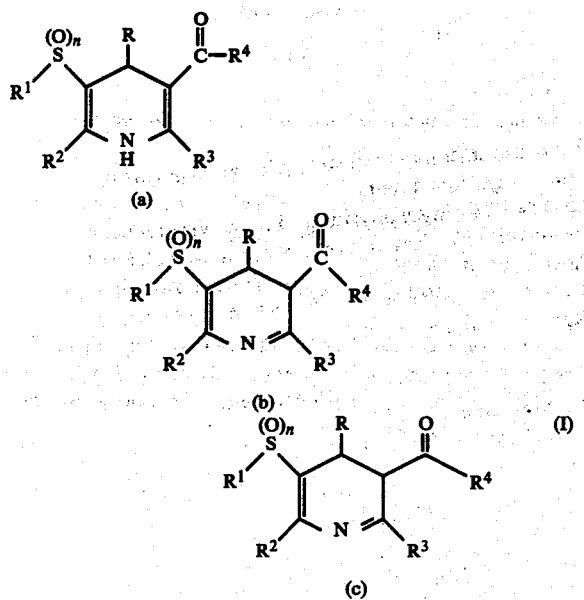

in which

R represents an aryl radical or a thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl or quinoxalyl radical, the aryl or the heterocyclic radical optionally containing from 1 to 3 identical or different substituents from phenyl, alkyl, alkenyl, alkinyl, alkoxy, alkenoxy, alkinoxy, alkylene, dioxyalkylene, halogen, trifluoromethyl, trifluoromethoxy, hydroxyl, amino, alkylamino, nitro, cyano, azido, carboxyl, carbalkoxy, carboxamido, sulphonamido or $SO_m$-alkyl (m=0 to 2), n denotes 0, 1 or 2, $R^1$ represents a straight-chain, branched or cyclic, saturated or unsaturated aliphatic hydrocarbon radical which is optionally interrupted by 1 or 2 oxygen atoms in the chain, or in which a hydrogen atom can be replaced by a hydroxyl group or by a phenoxy or phenyl group which is optionally substituted by halogen, cyano, amino, alkylamino, alkoxy, alkyl, trifluoromethyl or nitro, or replaced by an α-, β- or γ-pyridyl group or by an amino group, this amino group optionally carrying either hydrogen and one substituent or two identical or different substituents from alkyl, alkoxyalkyl, aryl and aralkyl groups and these substituents optionally forming, with the nitrogen atom, a 5-membered to 7-membered ring which can contain an oxygen, sulphur or nitrogen atom as a further hetero-atom, or represents an aryl radical which optionally contains 1 to 3 identical or different substituents from the group alkyl, alkoxy, halogen, cyano, trifluoromethyl, trifluoromethoxy, amino, alkylamino or nitro and $R^4$ represents alkyl, aryl, aralkyl or the group —$OR^5$, wherein $R^5$ represents a straight-chain, branched or cyclic, saturated or unsaturated hydrocarbon radical which is optionally interrupted by 1 or 2 oxygen atoms in the chain, or in which a hydrogen atom can be replaced by a hydroxyl group or by a phenoxy or phenyl group which is optionally substituted by halogen, cyano, amino, alkylamino, alkoxy, alkyl, trifluoromethyl or nitro, or by an α-, β- or γ-pyridyl group or by an amino group, this amino group optionally carrying either hydrogen and one substituent or two identical or different substituents from the group alkyl, alkoxy-alkyl, aryl and aralkyl and these substituents optionally forming, with the nitrogen atom, a 5-membered to 7-membered ring which can contain an oxygen, sulphur or nitrogen atom as a further hetero-atom, or represents an amino group which is optionally substituted by 1 or 2 identical or different substituents from the group hydrogen, alkyl, aryl or aralkyl, The substituents $R^2$ and $R^3$ in the tautomeric formulae Ia to Ic can have different meanings. The most important substituent combinations are defined as follows:

(A) $R^2$ denotes an amino group and $R^3$ denotes the radical

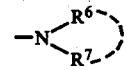

wherein $R^6$ represents hydrogen or an alkyl group and $R^7$ represents alkyl, aryl or aralkyl or $R^6$ and $R^7$ form together with the nitrogen atom, a 5-membered to 7-membered ring which is optionally interrupted by oxygen, sulphur or nitrogen, the nitrogen atom either carrying a hydrogen atom or a lower alkyl group.

(B) $R^2$ denotes the amino group and $R^3$ denotes the radical $R^8$, wherein $R^8$ represents hydrogen, a straight-chain or branched alkyl radical, an aryl radical or an aralkyl radical.

(C) $R^2$ denotes the group

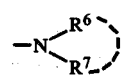

$R^3$ denotes the radical $R^8$, wherein $R^6$, $R^7$ and $R^8$ have the meaning indicated above.

(D) $R^2$ denotes the radical $R^8$, wherein $R^8$ has the meaning indicated above, and $R^3$ denotes the amino group.

Although the compounds of the invention exist in several tautomeric forms, for convenience individual compounds of the invention will be identified in this specification by single structural formulae. The individual formulae are however to be construed as including all tautomeric forms of the compounds.

The compounds according to the invention have a strong coronary action and anti-hypertensive properties.

Furthermore, it has been found that the new dihydropyridines are obtained when (A) ylidene compounds of the formula II $$R-CH=C\begin{smallmatrix}CN\\S-R^1\\(O)_n\end{smallmatrix} \quad (II)$$

in which

R, $R^1$ and n have the meaning indicated above, are reacted with endiaminocarbonyl compounds of the formula III $$\begin{smallmatrix}H_2N\\\phantom{-}R^6\\\phantom{-}R^7\end{smallmatrix}N-C=CH-COR^4 \quad (III)$$

in which $R^4$, $R^6$ and $R^7$ have the meaning indicated above, in water or in inert organic solvents, or (B) ylidene-β-dicarbonyl compounds of the formula IV $$R-CH=C\begin{smallmatrix}COR^4\\COR^3\end{smallmatrix} \quad (IV)$$

in which

R, $R^3$ and $R^4$ have the meaning indicated above, are reacted with endiaminosulphonyl compounds of the formula V $$\begin{smallmatrix}H_2N\\H_2N\end{smallmatrix}C=CH-S(O)_n-R^1 \quad (V)$$

in which $R^1$ and n have the meaning indicated above, in water or in inert organic solvents, or (C) ylidene-β-dicarbonyl compounds of the formula IV $$R-CH=C\begin{smallmatrix}COR^4\\COR^3\end{smallmatrix} \quad (IV)$$

in which

R, $R^3$ and $R^4$ have the meaning indicated above, are reacted with endiaminosulphonyl compounds of the formula VI $$\begin{smallmatrix}H_2N\\\phantom{-}R^6\\\phantom{-}R^7\end{smallmatrix}N-C=CH-S(O)_n-R^1 \quad (VI)$$

in which $R^1$, $R^6$, $R^7$ and n have the meaning indicated above, in water or in inert organic solvents, or (D) ylidene compounds of the formula VII $$R-CH=C\begin{smallmatrix}S(O)_n-R^1\\COR^2\end{smallmatrix} \quad (VII)$$

in which

R, $R^1$, $R^2$ and n have the meaning indicated above, are reacted with endiaminocarbonyl compounds of the formula VIII $$\begin{smallmatrix}H_2N\\H_2N\end{smallmatrix}C=CH-CO-R^4 \quad (VIII)$$

in which $R^4$ has the meaning indicated above, in water or in inert organic solvents.

The new 1,4-dihydropyridine derivatives according to the invention possess valuable pharmacological properties. Because of their influencing action on the circulatory system, they can be used as anti-hypertensive agents, as vasodilators and as coronary therapentic agents.

Depending on the nature of the starting materials used, the synthesis of the compounds according to the invention can be represented, by way of example, by the following equations:

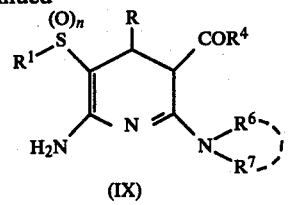

is reacted with endiaminocarbonyl compound of the formula III to give a dihydropyridine derivative of the formula IX.

In the formula II,

R preferably represents a phenyl or naphthyl radical or a thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl or quinoxalyl radical. The heterocyclic radicals mentioned and, in particular, the phenyl radical can contain 1 or 2 identical or different substituents, substituents which may be mentioned being, preferably, phenyl, straight-chain or branched alkyl with 1 to 8, in particular 1 to 4, carbon atoms, cycloalkyl with 3 to 7 carbon atoms, alkenyl or alkinyl with 2 to 6 carbon atoms, in particular 2 to 3 carbon atoms, alkoxy with preferably 1 to 4, in particular 1 to 2, carbon atoms, alkanoxy and alkinoxy with 2 to 6, in particular 3 to 5, carbon atoms, dioxymethylene, halogen, such as fluorine, chlorine, bromine or iodine, especially fluorine, chlorine or bromine, trifluoromethyl, trifluoromethoxy, nitro, cyano, azido, hydroxyl, amino, monoalkylamino and dialkylamino with preferably 1 to 4, in particular 1 or 2, carbon atoms per alkyl group, carboxyl, carbalkoxy with preferably 2 to 4, in particular 2 or 3 carbon atoms, carboxamido, sulphonamido or $SO_m$-alkyl, wherein m denotes a number from 0 to 2 and alkyl preferably contains 1 to 4, in particular 1 or 2, carbon atoms, n preferably represents 0, 1 or 2, in particular 2 and $R^1$ preferably represents a straight-chain, branched or cyclic, saturated or unsaturated aliphatic hydrocarbon radical with up to 8 C atoms, in particular with up to 4 C atoms, which is optionally interrupted by an oxygen atom in the chain, or in which a hydrogen atom can be replaced by a hydroxyl group or by a phenoxy or phenyl group which is optionally substituted by halogen, such as fluorine, chlorine or bromine, cuano, amino, monoalkylamino and dialkylamino with 1 to 2 carbon atoms per alkyl group in each case, alkoxy with 1 to 4 carbon atoms, alkyl with 1 to 4 carbon atoms, trifluoromethyl or nitro, or by an α-, β- or γ-pyridyl group or by an amino group, this amino group optionally carrying either hydrogen and one substituent or two identical or different substituents from the group alkyl with up to 4 carbon atoms, alkoxyalkyl with up to 4 carbon atoms, phenyl and aralkyl, in particular benzyl, and these substituents optionally forming, with the nitrogen atom, a 5-membered to 7-membered ring which can contain an oxygen, sulphur or nitrogen atom as a further heteroatom, the additional N atom carrying a hydrogen atom or a lower alkyl group, or represents an aryl radical, in particular a phenyl radical, which can optionally carry 1 to 2 identical or different substituents, substituents which may be mentioned being straight-chain or branched alkyl with 1 to 4 carbon

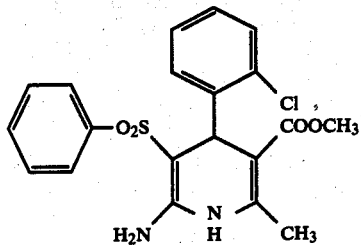
(C)

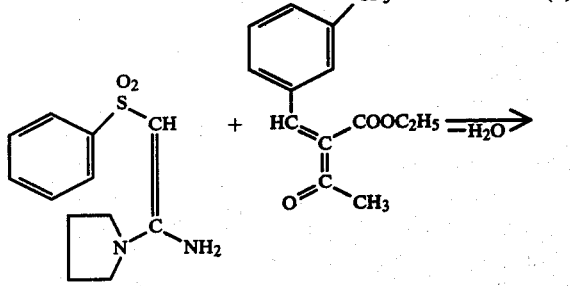

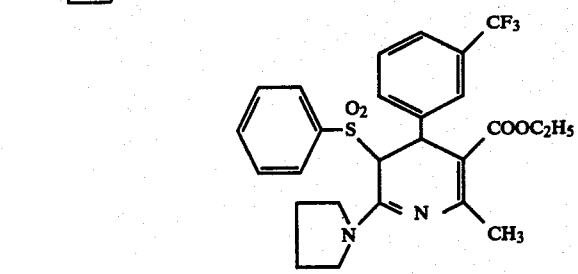
(D)

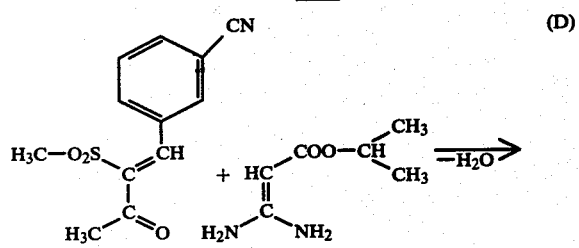

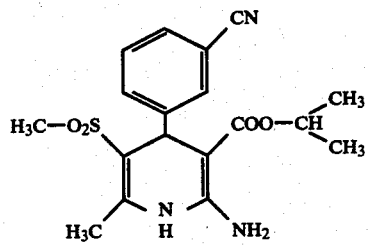

PROCESS VARIANT A

According to the procedure indicated under (A), an ylidene compound of the formula II

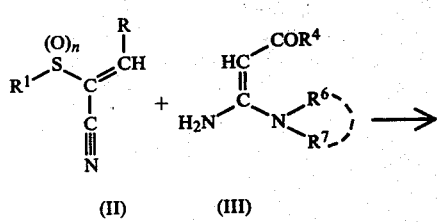

(II)   (III)

atoms, alkoxy with 1 to 2 carbon atoms, halogen, such as fluorine, chlorine or bromine, cyano, trifluoromethyl, trifluoromethoxy, amino, monoalkylamino and dialkylamino with 1 to 2 carbon atoms per alkyl group in each case or nitro.

The ylidene compounds of the formula II used as starting materials are known from the literature or can be prepared by methods known from the literature (compare G. Beck and D. Gunther, Chem. Ber. 106, 2,758 (1973)).

Examples which may be mentioned are: α-methylsulphonyl-β-phenyl-acrylonitrile, α-methylsulphonyl-β-(2'-nitrophenyl)-acrylonitrile, α-methylsulphonyl-β-(3'-nitrophenyl)-acrylonitrile, α-methylsulphonyl-β-(2'-trifluoromethylphenyl)-acrylonitrile, α-methylsulphonyl-β-(2'-cyanophenyl)-acrylonitrile, α-methylsulphonyl-β-(3'-cyanophenyl)-acrylonitrile, α-methylsulphonyl-β-(2'-methoxyphenyl)-acrylonitrile, α-methyl-sulphonyl-β-(2'-cyclopropylmethyloxyphenyl)-acrylonitrile, α-methylsulphonyl-β-(2'-propargyloxyphenyl)-acrylonitrile, α-methylsulphonyl-β-(2'-chlorophenyl)-acrylonitrile, α-ethylsulphonyl-β-(2'-nitrophenyl)-acrylonitrile, α-n-butylsulphonyl-β-(3'-nitrophenyl)-acrylonitrile, α-cyclopentylsulphonyl-β-(2'-trifluoromethylphenyl)-acrylonitrile, α-(2-methoxyethylsulphonyl)-β-(3'-nitrophenyl)-acrylonitrile, α-(2-dimethylaminoethylsulphonyl)-β-(2'-cyanophenyl)-acrylonitrile, α-(2-(piperidino-1)-ethylsulphonyl)-β-(3'-chlorophenyl)-acrylonitrile, α-(2-(N-benzyl-N-methylamino)-ethylsulphonyl)-β-(3'-nitrophenyl)-acrylonitrile, α-benzylsulphonyl-β-(2'-nitrophenyl)-acrylonitrile, α-(2-phenoxyethylsulphonyl)-β-(3'-nitrophenyl)-acrylonitrile, α-(2-(pyridyl-4)-ethylsulphonyl)-β-(3'-cyano-phenyl)-acrylonitrile, α-phenylsulphonyl-β-(2'-nitrophenyl)-acrylonitrile, α-(4-chlorophenylsulphonyl)-β-(2'-trifluoro-methylphenyl)-acrylonitrile, α-(4-methylphenylsulphonyl)-β-(3'-nitrophenyl)-acrylonitrile, α-(4-methoxyphenylsulphonyl)-β-(2'-chlorophenyl)-acrylonitrile, α-(4-nitrophenylsulphonyl)-β-(2'-trifluoromethoxyphenyl)-acrylonitrile, α-(4-trifluoromethylphenylsulphonyl)-β-(2'-nitrophenyl)-acrylonitrile, α-(3,4-dichlorophenylsulphonyl)-β-(3'-nitrophenyl)-acrylonitrile, α-methylsulphonyl-β-(pyridyl-2)-acrylonitrile, α-isobutylsulphonyl-β-(pyridyl-3)-acrylonitrile, α-phenylsulphonyl-β-(quinolyl-4)-acrylonitrile, α-methylsulphonyl-β-(thienyl-2)-acrylonitrile and α-ethylsulphonyl-β-(furyl-2)-acrylonitrile.

In the formula III, $R^4$ preferably represents a straight-chain or branched alkyl radical with 1 to 4 carbon atoms, a phenyl or benzyl radical or the group —$OR^5$, wherein $R^5$ represents a straight-chain, branched or cyclic, saturated or unsaturated hydrocarbon radical with up to 8 carbon atoms which is optionally interrupted by an oxygen atom in the chain, or in which a hydrogen atom can be replaced by a hydroxyl group or by a phenoxy or phenyl group which is optionally substituted by halogen, such as fluorine, chlorine or bromine, cyano, amino, monoalkylamino and dialkylamino with 1 to 2 carbon atoms per alkyl group in each case, alkoxy with 1 to 4 carbon atoms, alkyl with 1 to 4 carbon atoms, trifluoromethyl or nitro, or by an α-, β- or γ-pyridyl or by an amino group, this amino group optionally carrying either hydrogen and one substituent or two identical or different substituents from the group alkyl with up to 4 carbon atoms, alkoxyalkyl with up to 4 carbon atoms, phenyl and aralkyl, in particular benzyl, and these substituents optionally forming, with the nitrogen atom, a 5-membered to 7-membered ring which can contain an oxygen, sulphur or nitrogen atom as a further hetero-atom, the additional nitrogen atom carrying a hydrogen atom or a lower alkyl group, or represents an amino group which is optionally substituted by 1 or 2 identical or different substituents from the group hydrogen, alkyl with up to 4 carbon atoms, phenyl or benzyl, $R^6$ preferably represents hydrogen or a straight-chain or branched alkyl radical with 1 to 4 carbon atoms and $R^7$ preferably represents a straight-chain or branched alkyl radical with 1 to 4 carbon atoms or a phenyl radical or a benzyl radical or $R^6$ and $R^7$ represent, together with the nitrogen atom, a 5-membered to 7-membered ring which is optionally interrupted by an oxygen or sulphur atom or by the NH or N-alkyl group, it being possible for the N-alkyl group to contain up to 4, in particular 1 or 2, carbon atoms.

The endiaminocarbonyl compounds of the formula III used as starting materials are known or can be prepared by known methods (compare, for example, German Offenlegungsschrift (German Published Specification) No. 2,239,815, publication date: 21.2.1974).

Examples which may be mentioned are: 3-amino-3-methylamino-acrylic acid methyl ester, 3-amino-3-dimethylaminoacrylic acid ethyl ester, 3-amino-3-dimethylamino-acrylic acid n-butyl ester, 3-amino-3-dimethylamino-acrylic acid isopropyl ester, 3-amino-3-dimethylamino-acrylic acid cyclopentyl ester, 3-amino-3-dimethylamino-acrylic acid β-methoxyethyl ester, 3-amino-3-dimethylamino-acrylic acid benzyl ester, 3-amino-3-dimethylamino-acrylic acid 4-chlorobenzyl ester, 3-amino-3-dimethylamino-acrylic acid β-phenoxyethyl ester, 3-amino-3-dimethylamino-acrylic acid β-(pyridyl-2)-ethyl ester, 3-amino-3-dimethylamino-acrylic acid β-dimethylamino-ethyl ester, 3-amino-3-dimethylamino-acrylic acid amide, 3-amino-3-dimethylamino-acrylic acid dimethylamide, 3-amino-3-methylethylamino-acrylic acid ethyl ester, 3-amino-3-isopropylamino-acrylic acid ethyl ester, 3-amino-3-anilino-acrylic acid ethyl ester, 3-amino-3-benzylamino-acrylic acid ethyl ester, 3-amino-3-N-pyrrolidino-acrylic acid ethyl ester, 3-amino-3-N-piperidino-acrylic acid ethyl ester, 3-amino-3-N-morpholino-acrylic acid isopropyl ester, 3-amino-3-N-thiomorpholino-acrylic acid isopropyl ester and 3-amino-3-N-N'-methylpiperazino-acrylic acid isopropyl ester.

The endiaminocarbonyl compounds of the formula III can be employed either in the free form or in the form of their salts (for example as hydrohalides). They are liberated from the salts with basic agents, such as, preferably, alkanolates.

A resulting basic compound can be converted into a corresponding acid addition salt, for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia, an alcoholate or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicyclic, aminosalicylic, embonic, nicotinic, methanesulfonic, ethanesulfonic, hydroxy-ethanesulfonic, ethylenesulfonic, benzenesulfonic, halogenbenzenesulfonic, toluenesulfonic, naphthalenesulfonic and sulfanilic acid; methionine, tryptophan, lysine and arginine.

These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

Diluents which can be used are all the inert organic solvents. These include, preferably, alcohols, such as ethanol, methanol and isopropanol, ethers, such as dioxane, diethyl ether, tetrahydrofurane, glycol monomethyl ether and glycol dimethyl ether, or glacial acetic acid, dimethylformamide, dimethylsulphoxide, acetonitrile, pyridine and hexamethylphosphoric acid triamide.

The reaction temperatures can be varied within a fairly wide range. In general, the reaction is carried out between about 20° C. and 150° C., preferably at the boiling point of the particular solvent.

The reaction can be carried out under normal pressure, but also under increased pressure. In general, the reaction is carried out under normal pressure.

In carrying out the process according to the invention, one mole of the ylidene compound of the formula II is preferably reacted per mol of endiaminocarbonyl compound of the formula III (if appropriate after liberation from a hydrohalide with a basic auxiliary) in a suitable solvent. The isolation and purification of the substances according to the invention is preferably carried out by distilling off the solvent in vacuo, if appropriate after separating off insoluble materials, and re-crystallising the residue, if appropriate obtained in the crystalline form only after cooling with ice, from a suitable solvent.

PROCESS VARIANT B

According to the procedure indicated under (B), a ylidene-β-dicarbonyl compound of the formula IV

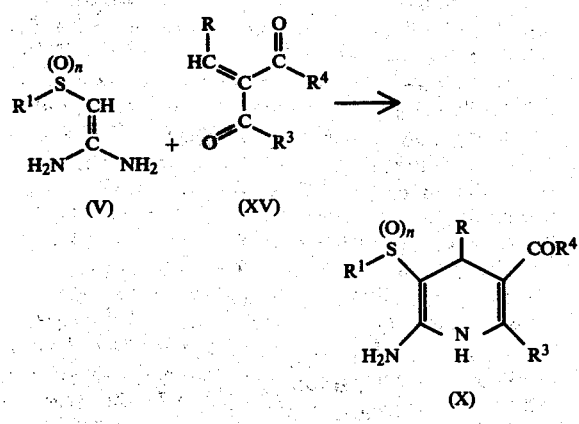

is reacted with an endiaminosulphonyl compound of the formula V to give a dihydropyridine derivative of the formula X.

In the formula V, $R^1$ and n have the meaning indicated under Process Variant (A).

The endiaminosulphonyl compounds of the formula V used as starting materials have not yet hitherto been described, but can be obtained according to methods known from the literature by reacting sulphonylacetic acid imide esters of the formula XI or XII

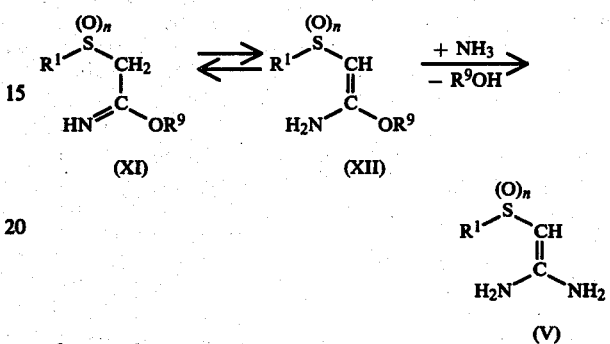

($R^9$ = lower alkyl)

with ammonia (compare, for example, S. R. Sandler and W. Kato, Org. Functional Group Preparations, Vol. III, 205 et seq., Acad. Press 1972).

Examples which may be mentioned are: 1,1-diamino-2-methylsulphonyl-ethylene, 1,1-diamino-2-n-butylsulphonyl-ethylene, 1,1-diamino-2-isopropylsulphonyl-ethylene, 1,1-diamino-2-cyclopentylsulphonyl-ethylene, 1,1-diamino-2-(2-methoxyethylsulphonyl)-ethylene, 1,1-diamino-2-(2-dimethylaminoethylsulphonyl)-ethylene, 1,1-diamino-2-(2-(piperidino-1)-ethylsulphonyl)-ethylene, 1,1-diamino-2-(2-(N-benzyl-N-methylamino)-ethylsulphonyl)-ethylene, 1,1-diamino-2-benzylsulphonyl-ethylene, 1,1-diamino-2-(2-phenoxyethylsulphonyl)-ethylene, 1,1-diamino-2-(2-(pyridyl-4)-ethylsulphonyl)-ethylene, 1,1-diamino-2-phenylsulphonyl-ethylene, 1,1-diamino-2-(4-chlorophenylsulphonyl)-ethylene, 1,1-diamino-2-(3-methyl-phenylsulphonyl)-ethylene, 1,1-diamino-2-(4-methoxyphenylsulphonyl)-ethylene, 1,1-diamino-2-(4-nitrophenylsulphonyl)-ethylene, 1,1-diamino-2-(4-trifluoromethylphenylsulphonyl)-ethylene, 1,1-diamino-2-(3,4-dichlorophenylsulphonyl)-ethylene and 1,1-diamino-2-(3-chloro-4-methylphenylsulphonyl)-ethylene.

In the formula IV, R and $R^4$ have the meaning indicated under process variant (A).

$R^3$ preferably represents hydrogen, a straight-chain or branched alkyl radical with 1 to 4, in particular 1 to 2, carbon atoms, a phenyl radical or a benzyl radical.

The ylidene-β-dicarbonyl compounds of the formula IV used as starting materials are known from the literature or can be prepared by methods known from the literature (compare Org. Reactions XV, 204 et seq. (1967)).

Examples which may be mentioned are: benzylideneacetylacetone, β,β-dibenzoylstyrene, 2'-nitrobenzylideneacetylacetone, 2'-nitrobenzylideneacetoacetic acid methyl ester, 3'-nitrobenzylideneacetoacetic acid ethyl ester, 2'-trifluoromethylbenzylideneacetoacetic acid n-butyl ester, 2'-cyanobenzylideneacetoacetic acid isopropyl ester, 3'-cyanobenzylideneacetoacetic acid cyclopentyl ester, 2'-methylbenzylideneacetoacetic acid alkyl esters, 2'-methoxybenzylideneacetoacetic acid propargyl ester, 2'-propargyloxybenzylideneacetoacetic acid methyl ester, 2'-cyclopropylmethoxybenzylideneacetoacetic acid methyl ester, 2'-chlorobenzylideneacetoacetic acid 2-methoxyethyl ester, 3'-chlorobenzylideneacetoacetic acid 2-dimethylaminoethyl ester, 2'-bromobenzylideneacetoacetic acid 2-(piperidino-1)-ethyl ester, 2'-fluorobenzylideneacetoacetic acid 2-(N-benzyl-N-methylamino)-ethyl ester, 3'-trifluoromethoxybenzylideneacetoacetic acid propyl ester, 2'-ethinyl-benzylideneacetoacetic acid methyl ester, 3'-azidobenzylidene-acetoacetic acid ethyl ester, 4'-methoxycarbonylbenzylidene-acetoacetic acid n-butyl ester, 3'-methylsulphonylbenzylidene-acetoacetic acid isopropyl ester, 3'-methylsulphonylbenzylideneacetoacetic acid cyclohexyl ester, 2'-nitrobenzylidene-acetoacetic acid isobutyl ester, 3'-chloro-4'-nitrobenzylidene-acetoacetic acid benzyl ester, 4'-chloro-3'-sulphamoylbenzylideneacetoacetic acid 4-chlorobenzyl ester, 3',4'-dichlorobenzylideneacetoacetic acid 4-trifluoromethylbenzyl ester, 3'-cyanobenzylideneacetoacetic acid 2-phenoxyethyl ester, 2'-nitrobenzylideneacetoacetic acid 2-(pyridyl-2)-ethyl ester, 3'-nitrobenzylideneacetoacetic acid amide, 2'-trifluoromethyl-benzylideneacetoacetic acid dimethylamide, 2'-nitrobenzylidenepropionylacetic acid methyl ester, 2'-cyanobenzylidene-propionylacetic acid ethyl ester, 2'-trifluoromethylbenzyl-idenebenzoylacetic acid methyl ester, 3'-azidobenzylidene-α-phenylacetoacetic acid methyl ester, α-acetyl-β-(pyridyl-3)-acrylic acid methyl ester, α-acetyl-β-(quinolinyl-4)-acrylic acid 2-n-propoxyethyl ester, α-acetyl-β-(thionyl-2)-acrylic acid ethyl ester and α-acetyl-β-(furyl-2)-acrylic acid isobutyl ester.

The endiaminosulphonyl compounds of the formula V can be employed either in the free form or in the form of their salts (for example as hydrohalides). They are liberated from the salts with basic auxiliaries, such as, preferably, alkanolates.

Diluents which can be used are all the inert organic solvents. These include, preferably, alcohols, such as ethanol, methanol and isopropanol, ethers, such as dioxane, diethyl ether, tetrahydrofurane, glycol monomethyl ether and glycol dimethyl ether, or glacial acetic acid, dimethylformamide, dimethylsulphoxide, acetonitrile, pyridine and hexamethylphosphoric acid triamide.

The reaction temperatures can be varied within a fairly wide range. In general, the reaction is carried out at between about 20° C. and 150° C., preferably at the boiling point of the particular solvent.

The reaction can be carried out under normal pressure, but also under elevated pressure. In general, the reaction is carried out under normal pressure.

In carrying out the process according to the invention, preferably, one mol of the ylidene-β-dicarbonyl compound of the formula IV is reacted per mol of endiaminosulphonyl compound of the formula V (if appropriate after liberation from a hydrohalide with a basic auxiliary) in a suitable solvent. The isolation and purification of the substances according to the invention is preferably carried out by distilling off the solvent in vacuo, if appropriate after separating off insoluble materials, and recrystallising the residue, if appropriate obtained in the crystalline form only after cooling with ice, from a suitable solvent.

PROCESS VARIANT C

According to the procedure indicated under (C), anylidene-β-dicarbonyl compound of the formula IV

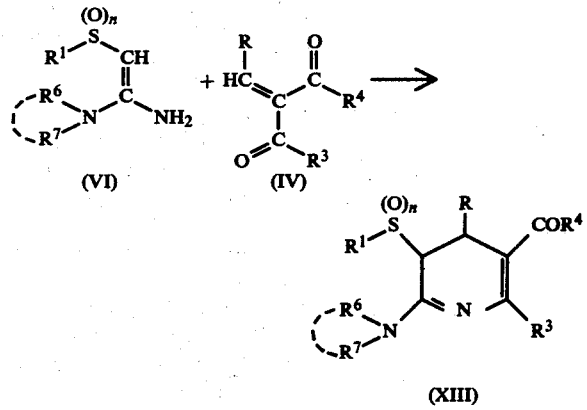

is reacted with an endiaminosulphonyl compound of the formula VI to give a dihydropyridine derivative of the formula XIII.

In the formula VI, $R^1$ and n as well as $R^6$ and $R^7$ have the meaning indicated under process variant (A).

The endiaminosulphonyl compounds of the formula VI used as starting materials have not yet hitherto been described, but can be obtained according to methods known from the literature by reacting sulphonylacetic acid imide esters of the formula XI or XII

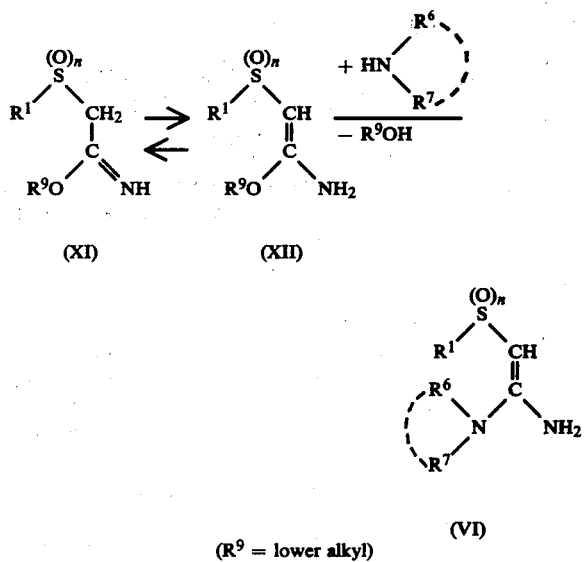

($R^9$ = lower alkyl)

with amines (compare, for example, S. P. Sandler and W. Kato, Org. Functional Group Preparations, Vol. III, 205 et seq., Acad. Press 1972).

Examples which may be mentioned are: 1-amino-1-dimethylamino-2-methylsulphonyl-ethylene, 1-amino-1-diethylamino-2-methylsulphonyl-ethylene, 1-amino-1-methylethylamino-2-n-butylsulphonyl-ethylene, 1-amino-1-methylamino-2-methylsulphonyl-ethylene, 1-amino-1-isopropylamino-2-methylsulphonyl-ethylene, 1-amino-1-anilino-2-methylsulphonyl-ethylene, 1-amino-1-benzylamino-2-methylsulphonyl-ethylene, 1-amino-1-N-pyrrolidino-2-methylsulphonyl-ethylene, 1-amino-1-N-piperidino-2-methylsulphonyl-ethylene, 1-amino-1-N-morpholino-2-methylsulphonyl-ethylene, 1-amino-1-N'-methylpiperazino-2-methylsulphonyl-ethylene, 1-amino-1-dimethylamino-2-isopropylsulphonyl-ethylene, 1-amino-1-dimethylamino-2-cyclopentylsulphonyl-ethylene, 1-amino-1-dimethylamino-2-(β-methoxyethyl)-sulphonyl-ethylene, 1-amino-1-dimethylamino-2-benzylsulphonyl-ethylene, 1-amino-1-dimethylamino-(β-phenoxyethyl)-sulphonyl-ethylene, 1-amino-1-dimethylamino-2-phenylsulphonylethylene, 1-amino-1-dimethylamino-2-(4-chlorophenylsulphonyl)-ethylene, 1-amino-1-dimethylamino-2-(4-methylphenylsulphonyl)-ethylene, 1-amino-1-dimethylamino-2-(4-methoxyphenylsulphonyl)-ethylene, 1-amino-1-dimethylamino-2-(4-trifluoromethylphenylsulphonyl)-ethylene, 1-amino-1-dimethylamino-2-(4-nitrophenylsulphonyl)-ethylene, 1-amino-1-N-pyrrolidino-2(3,4-dichloro-phenylsulphonyl)-ethylene and 1-amino-1-N-pyrrolidino-2-(3-chloro-4-methylphenylsulphonyl)-ethylene.

In the formula IV, R and $R^4$ have the meaning indicated under Process Variant (A) and $R^3$ has the meaning indicated under Process Variant (B).

Examples of the ylidene-β-dicarbonyl compounds of the formula IV used as starting materials are listed under Process Variant (B).

The endiaminosulphonyl compounds of the formula VI can be employed either in the free form or in the form of their salts (for example as hydrohalides). They are liberated from the salts with basic agents, such as, preferably, alkanolates.

Diluents which can be used are all the inert organic solvents. These include, preferably, alcohols, such as ethanol, methanol and isopropanol, ethers, such as dioxane, diethyl ether, tetrahydrofurane, glycol monomethyl ether and glycoldimethyl ether, or glacial acetic acid, dimethylformamide, dimethylsulphoxide, acetonitrile, pyridine and hexamethylphosphoric acid trimaide.

The reaction temperatures can be varied within a fairly wide range. In general, the reaction is carried out at between 20° C. and 150° C., preferably at the boiling point of the particular solvent.

The reaction can be carried out under normal pressure, but also under increased pressure. In general, the reaction is carried out under normal pressure.

In carrying out the process according to the invention, preferably, one mol of the ylidene-β-dicarbonyl compound of the formula IV is reacted per mole of endiaminosulphonyl compound of the formula VI (if appropriate after liberation from a hydrohalide with a basic auxiliary) in a suitable solvent. The isolation and purification of the substances according to the invention is preferably carried out by distilling off the solvent in vacuo, if appropriate after separating off insoluble materials, and recrystallising the residue, if appropriate obtained in the crystalline form only after cooling with ice, from a suitable solvent.

PROCESS VARIANT D

According to the procedure indicated under (D), a ylidene compound of the formula VII is reacted with an endiaminocarbonyl compound of the formula VIII to give a dihydropyridine derivative of the formula XIV.

In the formula VII, R, $R^1$ and n have the meaning indicated under Process Variant (A).

$R^2$ represents hydrogen, a straight-chain or branched alkyl radical with 1 to 4, in particular 1 to 2, carbon atoms, a phenyl radical or a benzyl radical.

The ylidene compounds of the formula VII used as starting materials are known from the literature or can be prepared by methods known from the literature (compare, for example, G. Beck and D. Gunther, Chem. Ber. 106, 2,758 et seq. (1973)).

Examples which may be mentioned are: 1-phenyl-2-methylsulphonyl-but-1-en-3-one, 1-(2'-nitrophenyl)-2-methylsulphonyl-but-1-en-3-one, 1-(3'-nitrophenyl)-2-ethylsulphonyl-but-1-en-3-one, 1-(2'-trifluoromethylphenyl)-2-methylsulphonyl-but-1-en-3-one, 1-(2'-cyanophenyl)-2-methylsulphonyl-but-1-en-3-one, 1-(2'-methylphenyl)-2-methylsulphonyl-but-1-en-3-one, 1-(2'-methoxyphenyl)-2-methylsulphonyl-but-1-en-3-one, 1-(2'-chlorophenyl)-2-methylsulphonyl-but-1-en-3-one, 1-(3'-cyanophenyl)-2-n-butylsulphonyl-but-1-en-3-one, 1-(2'-nitrophenyl)-2-(2-methoxyethylsulphonyl)-but-1-en-3-one, 1-(3'-nitrophenyl)-2-cyclopentylsulphonyl-but-1-en-3-one, 1-(2'-trifluoromethylphenyl)-2-(2-dimethylaminoethylsulphonyl)-but-1-en-3-one, 1-(2'-cyanophenyl)-2-(2-(piperidino-1)-ethylsulphonyl)-but-1-en-3-one, 1-(2'-nitrophenyl)-2-(2-(N-benzyl-N-methylamino)-ethylsulphonyl)-but-1-en-3-one, 1-(3'-nitrophenyl)-2-benzyl-sulphonyl-but-1-en-3-one, 1-(3'-cyanophenyl)-2-(2-phenoxy-ethylsulphonyl)-but-1-en-3-one, 1-(3'-nitrophenyl)-2-(2-(pyridyl-2)-ethylsulphonyl)-but-1-en-3-one, 1-(2'-trifluoro-methylphenyl)-2-phenylsulphonyl-but-1-en-3-one, 1-(2'-nitrophenyl)-2-(3-chlorophenylsulphonyl)-but-1-en-3-one, 1-(3'-nitrophenyl)-2-(4-methylphenylsulphonyl)-but-1-en-3-one, 1-(3'-nitrophenyl)-2-(4-methoxyphenylsulphonyl-but-1-en-3-one, 1-(2'-trifluoromethylphenyl)-2-(4-nitrophenylsulphonyl)-but-1-en-3-one, 1-(2'-nitrophenyl)-2-(4-trifluoromethylphenyl-sulphonyl)-but-1-en-3-one, 1-(2'-nitrophenyl)-2-methylsulphonyl-pent-1-en-3-one, 1-(3'-nitrophenyl-2-methylsulphonyl-4-phenyl-but-1-en-3-one, 1-(2'-nitrophenyl)-2-phenylsulphonyl-3-phenyl-prop-1-en-3-one; 1-(pyridyl-3)-2-methylsulphonyl-but-1-en-3-one, 1-(pyridyl-2)-2-n-butylsulphonyl-but-1-en-3-one, 1-(pyridyl-3)-2-phenylsulphonyl-but-1-en-3-one, 1-(quinolinyl-4)-2-methylsulphonyl-but-1-en-3-one, 1-(thienyl-2)-2-(4-trifluoromethylphenylsulphonyl)-but-1-en-3-one and 1-(furyl-2)-2-(3,4-dichlorophenylsulphonyl)-but-1-en-3-one.

In the formula VIII, $R^4$ has the meaning indicated under Process Variant (A).

The endiaminocarbonyl compounds of the formula VIII used as starting materials are already known or can be prepared by known methods (compare, for example, S. M. Mc Elvain and B. E. Tale, J. Amer. chem. Soc. 73, 2,760 et seq. (1951)).

Examples which may be mentioned are: 3,3-diamino-acrylic acid methyl ester, 3,3-diamino-acrylic acid ethyl ester, 3,3-diamino-acrylic acid n-butyl ester, 3,3-diamino-acrylic acid propyl ester, 3,3-diamino-acrylic acid cyclopentyl ester, 3,3-diamino-acrylic acid β-methoxyethyl ester, 3,3-diamino-acrylic acid benzyl ester, 3,3-diamino-acrylic acid 4-chlorobenzyl ester, 3,3-diamino-acrylic acid 4-methoxybenzyl ester, 3,3-diamino-acrylic acid β-phenoxyethyl ester, 3,3-diamino-acrylic acid β-(pyridyl-2)-ethyl ester, 3,3-diamino-acrylic acid β-dimethylaminoethyl ester, 3,3-diamino-acrylic acid amide and 3,3-diamino-acrylic acid dimethylamide.

The endiaminocarbonyl compounds of the formula X can be employed either in the free form or in the form of their salts (for example as hydrohalides). They are liberated from the salts with basic auxiliaries, such as, preferably alkanolates.

Diluents which can be used are all the inert organic solvents. These include, preferably, alcohols, such as ethanol, methanol and isopropanol, ethers, such as dioxane, diethyl ether, tetrahydrofurane, glycol monomethyl ether and glycol dimethyl ether, or glacial acetic acid, dimethylformamide, dimethylsulphoxide, acetonitrile, pyridine and hexamethylphosphoric acid triamide.

The reaction temperatures can be varied within a fairly wide range. In general, the reaction is carried out at between 20° C. and 150° C., preferably at the boiling point of the particular solvent.

The reaction can be carried out under normal pressure, but also under increased pressure. In general, the reaction is carried out under normal pressure.

In carrying out the process according to the invention, preferably one mol of the ylidene compound of the formula VII is reacted per mol of endiaminocarbonyl compound of the formula VIII (if appropriate after liberation from a hydrohalide with a basic auxiliary) in a suitable solvent. The isolation and purification of the substances according to the invention is preferably carried out by distilling off the solvent in vacuo, if appropriate after separating off insoluble materials, and re-crystallising the residue, if appropriate obtained in the crystalline form only after cooling with ice, from a suitable solvent.

The above preparation processes are only given for illustration and the preparation of the compounds of the formula I is not limited to these processes but any modification of these processes can be used in a similar manner for the preparation of the compounds according to the invention.

Depending on the choice of the starting substances, the compounds according to the invention can exist in stereoisomeric forms which either behave as mirror images (enantiomers) or do not behave as mirror images (diastereomers). The present invention relates to both the antipodes and the racemic forms as well as the diastereomer mixtures. The racemic forms, as also the diastereomers, can be separated into the stereoisomerically uniform constituents in a known manner (compare, for example, E. L. Eliel, Stereochemistry of Carbon Compounds, McGraw Hill, 1962).

In addition to those given in the preparation examples, the following compounds according to the invention can be made in the analagous manner: 2-dimethylamino-4-(2'-nitrophenyl)-5-methylsulphonyl-6-amino-3,4-dihydropyridine-3-carboxylic acid ethyl ester, 2-pyrrolidino-4-(2'-nitrophenyl)-5-methylsulphonyl-6-amino-3,4-dihydropyridine-3-carboxylic acid methyl ester, 2-di-n-butylamino-4-(2'-trifluoromethylphenyl)-5-methylsulphonyl-6-amino-3,4-dihydropyridine-3-carboxylic acid methyl ester, 2-pyrrolidino-4-(2'-trifluoromethylphenyl)-5-methylsulphonyl-6-amino-3,4-dihydropyridine-3-carboxylic acid methyl ester, 2-dimethylamino-4-(2'-cyanophenyl)-5-phenylsulphonyl-6-amino-3,4-dihydropyridine-3-carboxylic acid isopropyl ester, 2-dimethylamino-4-(3'-nitrophenyl)-5-(4-chlorophenylsulphonyl)-6-amino-3,4-dihydropyridine-3-carboxylic acid methyl ester, 2-methyl-4-(2'-nitrophenyl)-5-methylsulphonyl-6-amino-1,4-dihydro-pyridine-3-carboxylic acid ethyl ester, 2-methyl-4-(2'-methyl-phenyl)-5-methylsulphonyl-6-amino-1,4-dihydropyridine-3-carboxylic acid isopropyl ester, 2-methyl-4-(3'-nitrophenyl)-5-methylsulphonyl-6-amino-1,4-dihydropyridine-3-carboxylic acid cyclopentyl ester, 2-methyl-4-(3'-cyanophenyl)-5-methylsulphonyl-6-amino-1,4-dihydropyridine-3-carboxylic acid β-phenoxy-ethyl ester, 2-methyl-4-(2'-trifluoromethylphenyl)-5-methyl-sulphonyl-6-amino-1,4-dihydropyridine-3-carboxylic acid ethyl ester, 2-methyl-4-(2'-chlorophenyl)-5-methylsulphenyl-6-amino-1,4-dihydropyridine-3-carboxylic acid n-butyl ester, 2-ethyl-4-(2'-nitrophenyl)-5-phenylsulphonyl-6-amino-1,4-dihydropyridine-3-carboxylic acid ethyl ester, 2-ethyl-4-(2'-cyanophenyl)-5-phenylsulphonyl-6-amino-1,4-dihydropyridine-3-carboxylic acid methyl ester, 2-methyl-4-(2'-bromophenyl)-5-phenylsulphenyl-6-dimethylamino-4,5-dihydropyridine-3-carboxylic acid ethyl ester, 2-methyl-4-(2'-methoxyphenyl)-5-phenylsulphonyl-6-N-pyrrolidino-4,5-dihydropyridine-3-carboxylic acid ethyl ester, 2-methyl-4-(3'-nitrophenyl)-5-phenyl-sulphonyl-6-N-piperidino-4,5-dihydro-pyridine-3-carboxylic acid methyl ester, 2-amino-4-(3'-nitro-phenyl)-5-methylsulphonyl-6-methyl-1,4-dihydropyridine-3-carboxylic acid ethyl ester, 2-amino-4-(2'-nitrophenyl)-5-methylsulphonyl-6-methyl-1,4-dihydropyridine-3-carboxylic acid methyl ester, 2-amino-4-(3'-nitrophenyl)-5-ethylsulphonyl-6-methyl-1,4-dihydropyridine-3-carboxylic acid methyl ester, 2-amino-4-(2'-nitrophenyl)-5-methylsulphonyl-6-methyl-1,4-dihydropyridine-3-carboxylic acid isobutyl ester, 2-amino-4-(2'-nitrophenyl)-5-isobutylsulphonyl-6-methyl-1,4-dihydropyridine-3-carboxylic acid methyl ester, 2-amino-4-(2'-trifluoromethylphenyl)-5-ethylsulphonyl-6-methyl-1,4-dihydropyridine-3-carboxylic acid ethyl ester, 2-amino-4-(3'-cyanophenyl)-5-methylsulphonyl-6-methyl-1,4-dihydropyridine-3-carboxylic acid ethyl ester, 2-amino-4-(2'-chlorophenyl)-5-methylsulphonyl-6-methyl-1,4-dihydropyridine-3-carboxylic acid ethyl ester, 2-amino-4-(2'-methoxyphenyl)-5-methylsulphonyl-6-methyl-1,4-dihydropyridine-3-carboxylic acid isopropyl ester and 2-amino-4-(pyridyl-2)-5-ethylsulphonyl-6-methyl-1,4-dihydropyridine-3-carboxylic acid ethyl ester. Of particular importance are: amino-dihydropyridines of the formula I in which R represents a phenyl radical which is optionally substituted by nitro, cyano, halogen, trifluoromethyl, alkyl or alkoxy with 1 to 4 carbon atoms in each case, or represents a pyridyl radical, n represents 0 or 2, $R^1$ represents alkyl with 1 to 4 carbon atoms or phenyl which is optionally substituted by halogen, $R^2$ and $R^3$ are different from one another and each represents amino, alkyl with 1 to 2 carbon atoms or dialkylamino with 1 to 2 carbon atoms in the alkyl group in each case and $R^4$ represents the group $-OR^5$, wherein $R^5$ denotes straight-chain, branched or cyclic alkyl with up to 6 carbon atoms or wherein $R^5$ represents an alkoxyalkyl radical with up to 4 carbon atoms or a benzyl radical.

The new compounds are substances which can be used as medicaments. They have a broad and diverse spectrum of pharmacological action.

In detail, it was possible to demonstrate the following main actions in animal experiments:

(1) On parenteral, oral and perlingual administration the compounds produce a distinct and long-lasting dilation of the coronary vessels. This action on the coronary vessels is intensified by a simultaneous nitrile-like effect of reducing the load on the heart.

They influence or modify the heart metabolism in the sense of an energy saving.

(2) The excitability of the stimulus formation and excitation conduction system with the heart is lowered, so that an anti-fibrillation action which can be demonstrated at therapeutic doses results.

(3) The tons of the smooth muscle of the vessels is greatly reduced under the action of the compounds. This vascularspasmolytic action can take place in the entire vascular system or can manifest itself more or less isolated in circumscribed vascular regions (such as, for example, the central nervous system).

(4) The compounds lower the blood pressure of normotonic and hypertonic animals and can thus be used as anti-hypertensive agents.

(5) The compounds have strongly muscular-spasmolytic actions which manifest themselves on the smooth muscle of the stomach, the intestinal tract, the urogenital tract and the respiratory system.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile or isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The diluents to be used in pharmaceutical compositions (e.g. granulates) adapted to be formed into tablets, dragrees, capsules and pills include the following:

(a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bantonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above mentioned diluents.

The diluents to be used in pharmaceutical compositions adapted to be formed into suppositories can, for example, be the usual water-soluble or water-insoluble diluents, such as polyethylene glycols and fats (e.g. cocca oil and high esters [e.g. $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200 except in the presence of a surface active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, the solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention preferably contain about 0.1 to 99.5, more preferably from about 0.5 to 95% of the active ingredient by weight of the total composition.

In addition to a compound of the invention, the pharmaceutical compositions and medicaments according to the invention can also contain other pharmaceutically active compounds. They can also contain a plurality of compounds of the invention.

Any diluent in the medicaments of the present invention may be any of those mentioned above in relation to the pharmaceutical compositions of the present invention. Such medicaments can include solvents of molecular weight less than 200 as sole diluent.

The discrete coherent portions constituting the medicament according to the invention will generally be adapted, by virtue of their shape or packaging, for medical administration and can be, for example, any of the following: tablets (including lozenges and granulates), pills, dragees, capsules, suppositories and ampoules. Some of these forms can be made up for delayed release of the active ingredient. Some, such as capsules, include a protective envelope which renders the portions of the medicament physically discrete and coherent. Tablets can be scored to provide for the administration of fractional dosages.

The preferred daily dose for administration of the medicaments of the invention is about 0.5 mg to 2 g of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally or intravenously), rectally or locally, preferably orally or parenterally, especially perlingually or intravenously. Preferred pharmaceutical compositions and medicaments are therefore those adapted for oral or parenteral administration.

In general, it has proved advantageous, in the case of intravenous administration, to administer amounts of about 0.01 to 10 mg/kg, preferably about 0.05 to 5 mg/kg, of body weight daily to achieve effective results, and in the case of oral administration the dosage is about 0.05 to 20 mg/kg, preferably 0.5 to 5 mg/kg, of body weight daily.

Nevertheless it can at times be necessary to deviate from the amounts mentioned and in particular to do so as a function of the body weight of the test animal or of the nature of the administration method, but also because of the type of animal and its individual behaviour towards the medicament, or the nature of the formulation of the medicament and the time or interval at which it is administered. Thus it may suffice, in some cases, to manage with less than the above-mentioned minimum amount, whilst in other cases the upper limit mentioned must be exceeded. Where larger amounts are administered it can be advisable to divide these into several individual administrations over the course of the day.

PREPARATION EXAMPLES

Examples 1 to 6 illustrate process variant A

EXAMPLE 1

2-Dimethylamino-4-phenyl-5-methylsulphonyl-6-amino-3,4-dihydropyridine-3-carboxylic acid methyl ester

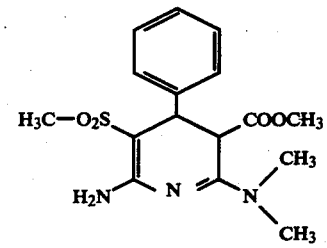

A solution of 2.3 g (0.1 mol) of sodium in 150 ml of ethanol was added dropwise to a suspension of 20.7 g (0.1 mol) of α-methylsulphonyl-β-phenyl-acrylontrile and 18.1 g (0.1 mol) of 3-amino-3-dimethylamino-acrylic acid methyl ester hydrochloride in 100 ml of ethanol at room temperature. The reaction mixture was then heated to the boil for 6 hours under nitrogen and filtered hot and the filtrate was concentrated to dryness in vacuo. The residue was taken up in a little ethanol, filtered off and recrystallised from ethanol.

Melting point: 150° C.; yield: 24.2 g (69%).

EXAMPLE 2

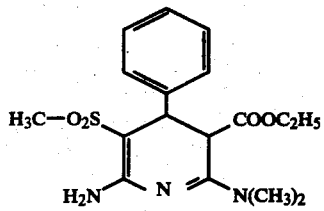

2-Dimethylamino-4-phenyl-5-methylsulphonyl-6-amino-3,4-dihydropyridine-3-carboxylic acid ethyl ester of melting point: 140° C. (ethanol) was obtained analogously to Example 1 from α-methylsulphonyl-β-phenyl-acrylonitrile and 3-amino-3-dimethyl-amino-acrylic acid ethyl ester hydrochloride in ethanol.

Yield: 65% of theory.

EXAMPLE 3

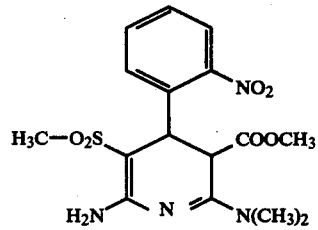

2-Dimethylamino-4-(2'-nitrophenyl)-5-methylsulphonyl-6-amino-3,4-dihydropyridine-3-carboxylic acid methyl ester of melting point: 180° C. (ethanol) was obtained analogously to Example 1 from α-methylsulphonyl-β-(2'-nitrophenyl)-acrylonitrile and 3-amino-3-dimethylamino-acrylic acid methyl ester hydrochloride in methanol. Yield: 65% of theory.

EXAMPLE 4

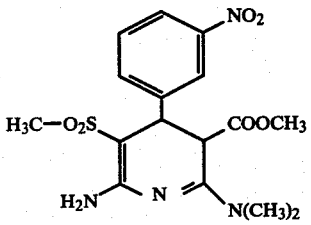

2-Dimethylamino-4-(3'-nitrophenyl)-5-methylsulphonyl-6-amino-3,4-dihydropyridine-3-carboxylic acid methyl ester of melting point: 214° C. (ethanol) was obtained analogously to Example 1 from α-methylsulphonyl-β-(3'-nitrophenyl)acrylo-nitrile and 3-amino-3-dimethylamino-acrylic acid methyl ester hydrochloride in methanol.

Yield: 72% of theory.

EXAMPLE 5

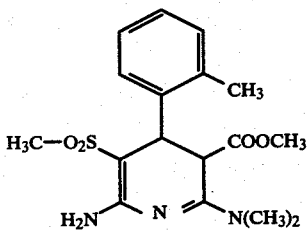

2-Dimethylamino-4-(2'-methylphenyl)-5-methylsulphonyl-6-amino-3,4-dihydropyridine-3-carboxylic acid methyl ester of melting point: 169° C. (ethanol) was obtained analogously to Example 1 from α-methylsulphonyl-β-(2'-methylphenyl)acrylo-nitrile and 3-amino-3-dimethylamino-acrylic methyl ester hydrochloride in methanol.

Yield: 78% of theory.

EXAMPLE 6

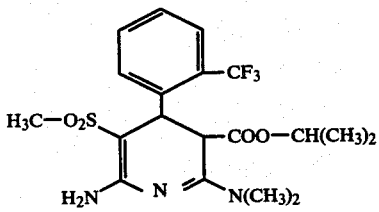

2-Dimethylamino-4-(2'-trifluoromethylphenyl)-5-methylsulphonyl-6-amino-3,4-dihydropyridine-3-carboxylic acid isopropyl ester of melting point: 126° C. (ethanol) was obtained analogously to Example 1 from α-methylsulphonyl-β-(2'-trifluoromethylphenyl)-acrylonitrile and 3-amino-3-dimethylaminoacrylic acid isopropyl ester hydrochloride in ethanol.

Yield: 55% of theory.

Examples 7 to 11 illustrate process variant B

EXAMPLE 7

2-Methyl-4-(2'-nitrophenyl)-5-phenylsulphonyl-6-amino-1,4-dihydropyridine-3-carboxylic acid methyl ester.

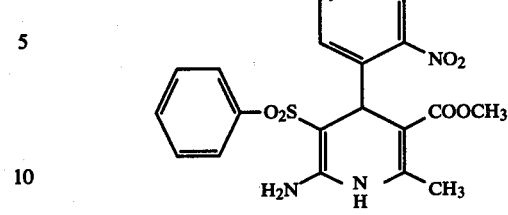

A solution of 1.15 g (50 mmols) of sodium in 50 ml of ethanol was added dropwise to a suspension of 12.5 g (50 mmols) of 2'-nitrobenzylideneacetoacetic acid methyl ester and 11.7 g (50 mmoles) of 1,1-diamino-2-phenylsulphonylethylene hydrochloride in 50 ml of ethanol at room temperature. The reaction mixture was then heated to the boil for 6 hours under nitrogen and filtered hot and the filtrate was concentrated to dryness in vacuo. The residue was suspended in ethanol, filtered off and recrystallised from ethanol.

Melting point: 241° C.; yield: 11.4 g (53%).

EXAMPLE 8

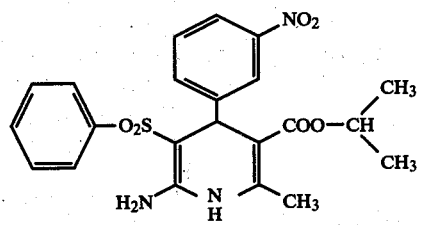

2-Methyl-4-(3'-nitrophenyl)-5-phenylsulphonyl-6-amino-1,4-dihydropyridine-3-carboxylic acid isopropyl ester of melting point: 185° C. (ethanol) was obtained analogously to Example 7 from 3'-nitrobenzylideneacetoacetic acid isopropyl ester and 1,1-diamino-2-phenylsulphonylethylene hydrochloride in ethanol.

Yield: 49% of theory.

EXAMPLE 9

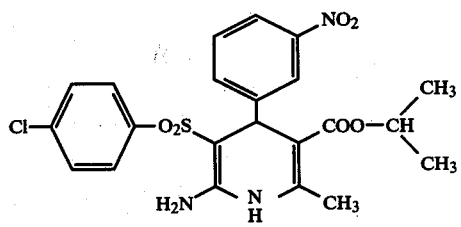

2-Methyl-4-(3'-nitrophenyl)-5-(4'''-chlorophenylsulphonyl)-6-amino-1,4-dihydropyridine-3-carboxylic acid isopropyl ester of melting point: 222° C. (ethanol) was obtained analogously to Example 7 from 3'-nitrobenzylideneacetoacetic acid isopropyl ester and 1,1-diamino-2-(4-chlorophenylsulphonyl)ethylene hydrochloride in ethanol. Yield: 40% of theory.

EXAMPLE 10

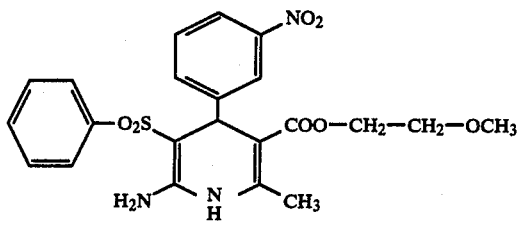

2-Methyl-4-(3'-nitrophenyl)-5-phenylsulphonyl-6-amino-1,4-dihydropyridine-3-carboxylic acid 2-methoxyethyl ester of melting point: 160° C. (ethanol) was obtained analogously to Example 7 from 3'-nitrobenzylideneacetoacetic acid 2-methoxyethyl ester and 1,1-diamino-2-phenylsulphonyl-ethylene hydrochloride in ethanol. Yield: 54% of theory.

EXAMPLE 11

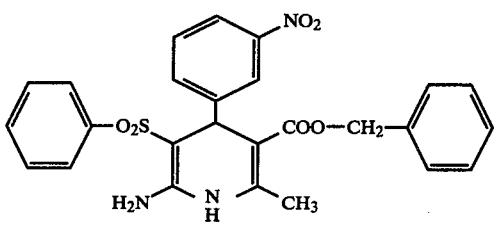

2-Methyl-4-(3'-nitrophenyl)-5-phenylsulphonyl-6-amino-1,4-dihydropyridine-3-carboxylic acid benzyl ester of melting point: 217° C. (ethanol) was obtained analogously to Example 7 from 3'-nitrobenzylideneacetoacetic acid benzyl ester and 1,1-diamino-2-phenylsulphonyl-ethylene hydrochloride in ethanol. Yield: 47% of theory.

Examples 12 to 14 illustrate process variant C.

EXAMPLES 12 TO 14.

2-Methyl-4-(2'-nitrophenyl)-5-phenylsulphonyl-6-dimethylamino-4,5-dihydropyridine-3-carboxylic acid methyl ester

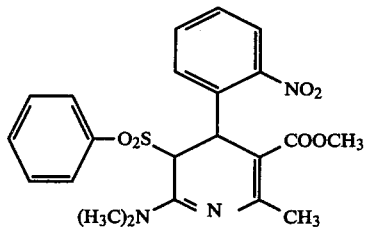

A solution of 1.15 g (50 mmols) of sodium in 50 ml of ethanol was added dropwise to a suspension of 12.5 g (50 mmols) of 2'-nitrobenzylideneacetoacetic acid methyl ester and 13.1 g (50 mmols) of 1-amino-1-dimethylamino-2-phenylsulphonylethylene hydrochloride in 50 ml of ethanol at room temperature. The reaction mixture was then heated to the boil for 6 hours under nitrogen and filtered hot and the filtrate was concentrated to dryness in vacuo. The residue was suspended in ethanol, filtered off and recrystallized from ethanol.

Melting point: 193° C.; yield: 12.5 g (55%).

EXAMPLE 13

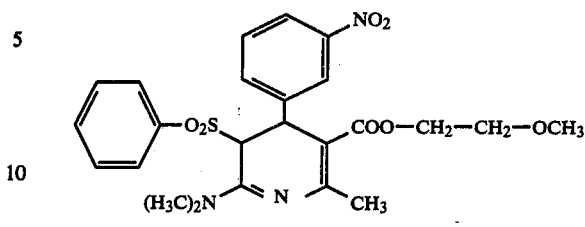

2-Methyl-4-(3'-nitrophenyl)-5-phenylsulphonyl-6-dimethylamino-4,5-dihydropyridine-3-carboxylic acid 2-methoxyethyl ester of melting point: 91° C. (ethanol) was obtained analogously to Example 12 from 3'-nitrobenzylideneacetoacetic acid 2-methoxyethyl ester and 1-amino-1-dimethylamino-2-phenylsulphonyl-ethylene hydrochloride in ethanol.

Yield: 44% of theory.

EXAMPLE 14

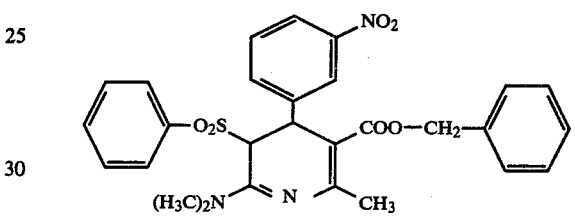

2-Methyl-4-(3'-nitrophenyl)-5-phenylsulphonyl-6-dimethylamino-4,5-dihydropyridine-3-carboxylic acid benzyl ester of melting point: 109° C. (ethanol) was obtained analogously to Example 12 from 3'-nitrobenzylideneacetoacetic acid benzyl ester and 1-amino-1-dimethylamino-2-phenylsulphonyl-ethylene hydrochloride in ethanol. Yield: 40% of theory.

Examples 15 to 21 illustrate process variant D.

EXAMPLE 15

2-Amino-4-(2'-nitrophenyl)-5-methylsulphonyl-6-methyl-1,4-dihydropyridine-3-carboxylic acid ethyl ester

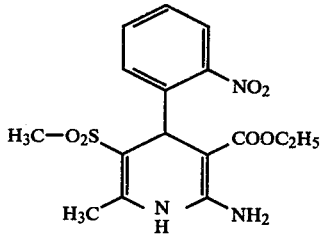

A solution of 1.15 g (50 mmols) of sodium in 50 ml of ethanol was added dropwise to a suspension of 13.5 g (50 mmols) of 1-(2'-nitrophenyl)-2-methylsulphonyl-but-1-en-3-one and 8.3 g (50 mmols) of 3,3-diaminoacrylic acid ethyl ester hydrochloride in 50 ml of ethanol at room temperature. The reaction mixture was then heated to the boil for 5 hours under nitrogen and filtered hot and the filtrate was concentrated to dryness in vacuo. The residue was suspended in ethanol, filtered off and recrystallised from ethanol.

Melting point: 205° C.; yield: 10.5 g (55%).

EXAMPLE 16

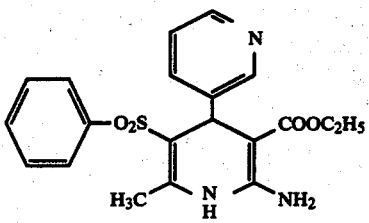

2-Amino-4-(pyridyl-3)-5-phenylsulphonyl-6-methyl-1,4-dihydropyridine-3-carboxylic acid ethyl ester of melting point: 252° C. (ethanol) was obtained analogously to Example 15 from 1-(pyridyl-3)-2-phenylsulphonyl-but-1-en-3-one and 3,3-diaminoacrylic acid ethyl ester hydrochloride in ethanol Yield: 50% of theory.

EXAMPLE 17

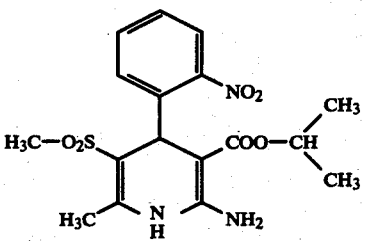

2-Amino-4-(2'-nitrophenyl)-5-methylsulphonyl-6-methyl-1,4-dihydropyridine-3-carboxylic acid isopropyl ester of melting point: 220° C. (ethanol) was obtained analogously to Example 15 from 1-(2'-nitrophenyl)-2-methylsulphonyl-but-1-en-3-one and 3,3-dimaino-carylic acid isopropyl ester hydrochloride in ethanol. Yield: 60% of theory.

EXAMPLE 18

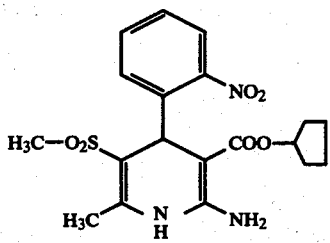

2-Amino-4-(2'-nitrophenyl)-5-methylsulphonyl-6-methyl-1,4-dihydropyridine-3-carboxylic acid cyclopentyl ester of melting point: 211° C. was obtained analogously to Example 15 from 1-(2'-nitrophenyl)-2-methylsulphonyl-but-1-en-3-one and 3,3-diaminoacrylic acid cyclopentyl ester hydrochloride in ethanol. Yield: 50% of theory.

EXAMPLE 19

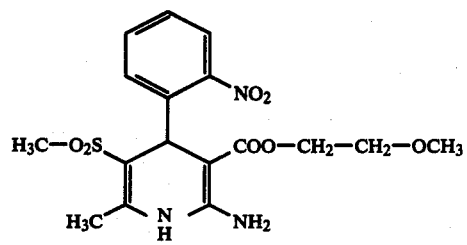

2-Amino-4-(2'-nitrophenyl)-5-methylsulphonyl-6-methyl-1,4-dihydropyridine-3-carboxylic acid 2-methoxyethyl ester of melting point: 157° C. (ethanol) was obtained analogously to Example 15 from 1-(2'-nitrophenyl)-2-methylsulphonyl-but-1-en-3-one and 3,3-diaminoacrylic acid 2-methoxyethyl ester hydrochloride in ethylene glycol monomethyl ether. Yield: 29% of theory.

EXAMPLE 20

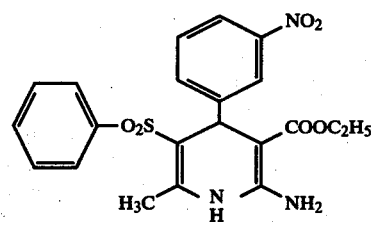

2-Amino-4-(3'-nitrophenyl)-5-phenylsulphonyl-6-methyl-1,4-dihydropyridine-3-carboxylic acid ethyl ester of melting point: 166° C. (ethanol) was obtained analogously to Example 15 from 1-(3'-nitrophenyl)-2-(4''-phenylsulphonyl)-but-1-en-3-one and 3,3-diaminoacrylic acid ethyl ester hydrochloride in ethanol. Yield: 55% of theory.

EXAMPLE 21

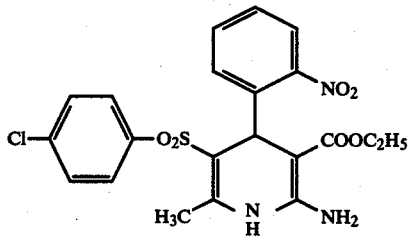

2-Amino-4-(2'-nitrophenyl)-5-(4''-chlorophenylsulphonyl)-6-methyl-1,4-dihydropyridine-3-carboxylic acid ethyl ester of melting point: 206° C. (ethanol) was obtained analogously to Example 15 from 1-(2'-nitrophenyl)-2-(4''-chlorophenylsulphonyl)-but-1-en-3-one, 3,3-diaminoacrylic acid ethyl ester hydrochloride in ethanol. Yield: 52% of theory.

What we claim is:
1. A sulphur-containing amino-dihydropyridine of the formula I (a), (b) or (c):

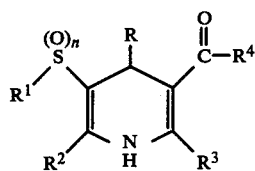

(a)

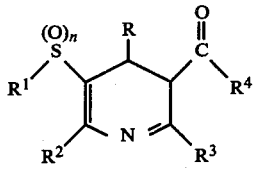

(b)

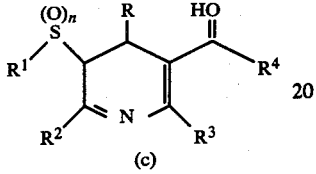

(c)

in which R represents a phenyl or naphthyl each of which is unsubstituted or substituted by 1 or 2 identical or different substituents selected from phenyl, straight-chain or branched alkyl with 1 to 8 carbon atoms, cycloalkyl with 3 to 7 carbon atoms, alkenyl or alkinyl with 2 to 6 carbon atoms, alkoxy with 1 to 4 carbon atoms, alkanoxy and alkinoxy radicals with 2 to 6 carbon atoms, dioxymethylene, fluorine, chlorine or bromine, trifluoromethyl, trifluoromethoxy, nitro, cyano, azido, hydroxyl, amino, monoalkylamino and dialkylamino radicals with 1 to 4 carbon atoms per alkyl group, carboxyl, carbalkoxy with 2 to 4 carbon atoms, carboxamido, sulphonamido and $SO_m$-alkyl, (wherein m denotes 0, 1 or 2 and the alkyl-group contains 1 to 4 carbon atoms,) and n denotes 0, 1 or 2, $R^1$ represents a straight-chain, branched or cyclic, saturated or unsaturated aliphatic hydrocarbon radical with up to 8 carbon atoms which is optionally interrupted by an oxygen atom in the chain, or in which a hydrogen atom is optionally replaced by a hydroxyl group or by a phenoxy or phenyl group which is optionally substituted by fluorine, chlorine or bromine, cyano, amino, monoalkylamino and dialkylamino with 1 to 2 carbon atoms per alkyl group in each case, alkoxy with 1 to 4 carbon atoms, alkyl with 1 to 4 carbon atoms, trifluoromethyl or nitro, or by an amino group, this amino group optionally carrying either hydrogen and one substituent or two identical or different substituents selected from alkyl with up to 4 carbon atoms, alkoxyalkyl with up to 4 carbon atoms, alkoxyalkyl with up to 4 carbon atoms, phenyl and benzyl, $R^2$ and $R^3$ are different from one another and each represents amino or dialkylamino with 1 to 2 carbon atoms in the alkyl group in each case and $R^4$ represents the group —$OR^5$, wherein $R^5$ represents a straight chain, branched or cyclic, saturated or unsaturated hydrocarbon radical with up to 8 carbon atoms which is optionally interrupted by an oxygen atom in the chain, or in which a hydrogen atom is optionally replaced by a hydroxyl group or by a phenoxy or phenyl group which is optionally substituted by fluorine, chlorine or bromine, cyano, amino, monoalkylamino and dialkylamino with 1 to 2 carbon atoms per alkyl group in each case, alkoxy with 1 to 4 carbon atoms, alkyl with 1 to 4 carbon atoms, trifluoromethyl or nitro, or by an amino group, this amino group optionally carrying either hydrogen and one substituent or two identical or different substituents selected from alkyl with up to 4 carbon atoms, a alkoxy-alkyl with up to 4 carbon atoms, phenyl and benzyl.

2. An amino-dihydropyridines of claim 1 in which

R represents a phenyl radical which is optionally substituted by nitro, cyano, halogen, trifluoromethyl, alkyl or alkoxy with 1 to 4 carbon atoms in each case, n represents 0 or 2, $R^1$ represents alkyl with 1 to 4 carbon atoms or phenyl which is optionally substituted by halogen, $R^2$ and $R^3$ are different from one another and each represents amino, alkyl with 1 to 2 carbon atoms or dialkylamino with 1 to 2 carbon atoms in the alkyl group in each case and $R^4$ represents the group —$OR^5$, wherein $R^5$ denotes straight-chain, branched or cyclic alkyl with 1 to 6 carbon atoms or wherein $R^5$ represents an alkoxyalkyl radical with 1 to 4 carbon atoms or a benzyl radical. herein.

3. A pharmaceutical composition for combatting cardiovascular diseases by vasodilation containing as an active ingredient, an effective amount therefor of a compound of claim 1 in admixture with a solid or liquified gaseous diluent or in admixture with a liquid diluent other than a solvent a molecular weight less than 200 except in the presence of a surface-active agent.

4. A pharmaceutical composition containing as an active ingredient an effective amount of a compound of claim 1 in the form of a sterile or isotonic aqueous solution.

5. A composition of claim 4 containing from 0.5 to 95% by weight of the said active ingredient.

6. A medicament in dosage unit form comprising an effective amount of a compound of claim 1 and an inert pharmaceutical carrier.

7. A medicament of claim 6 in the form of tablets, pills, dragees, capsules, ampoules, or suppositories.

8. A method of treating cardiovascular diseases in warm-blooded animals by vasodilation which comprises administering to the animals an effective amount of an active compound of claim 1 either alone or in admixture with a diluent or in the form of a medicament.

9. A method of claim 8 in which the active compound is administered in an amount of 0.01 to 20 mg per kg body weight per day.

10. A method of claim 8 in which the active compound is administered orally or parenterally.

11. A composition of claim 7 containing from 0.5 to 95% by weight of said active ingredient.

* * * * *